(12) United States Patent  
DeSmet et al.

(10) Patent No.: US 7,918,896 B2
(45) Date of Patent: Apr. 5, 2011

(54) UNITARY ACETABULAR CUP PROSTHESIS WITH EXTENSION FOR DEFICIENT ACETABULUM

(75) Inventors: Koen DeSmet, Heusden (BE); Steven F. Seyer, Germantown, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 1817 days.

(21) Appl. No.: 10/941,210

(22) Filed: Sep. 15, 2004

(65) Prior Publication Data

US 2006/0058887 A1    Mar. 16, 2006

(51) Int. Cl.
*A61F 2/32* (2006.01)

(52) U.S. Cl. .................................. 623/22.36

(58) Field of Classification Search .... 623/22.11–22.39, 623/18.11, 19.11, 19.12
See application file for complete search history.

(56) References Cited

U.S. PATENT DOCUMENTS

| 3,903,549 | A | | 9/1975 | Deyerle |
| 4,298,993 | A | * | 11/1981 | Kovaleva et al. ......... 623/22.36 |
| 4,801,300 | A | | 1/1989 | Kurze et al. |
| 4,919,675 | A | | 4/1990 | Dietschi |
| 5,314,488 | A | | 5/1994 | Hayashi et al. |
| 5,314,490 | A | | 5/1994 | Wagner |
| 5,370,704 | A | | 12/1994 | DeCarlo |
| 5,425,778 | A | | 6/1995 | Zichner |
| 5,702,477 | A | * | 12/1997 | Capello et al. ............. 623/22.21 |
| 5,928,288 | A | | 7/1999 | Wilson |
| 5,931,870 | A | * | 8/1999 | Cuckler et al. ............. 623/22.21 |
| 6,162,257 | A | | 12/2000 | Gustilo et al. |
| 6,224,633 | B1 | | 5/2001 | Kälberer et al. |
| 6,416,553 | B1 | * | 7/2002 | White et al. ............... 623/22.38 |
| 6,458,161 | B1 | * | 10/2002 | Gibbs et al. ............... 623/22.32 |
| 6,620,200 | B1 | * | 9/2003 | Descamps et al. ......... 623/22.32 |
| 6,908,486 | B2 | * | 6/2005 | Lewallen ................... 623/22.21 |

FOREIGN PATENT DOCUMENTS

| EP | 1236450 | 9/2002 |
| EP | 1336394 A1 | 8/2003 |
| FR | 2758255 A1 | 7/1998 |
| FR | 2831424 A3 | 5/2003 |
| GB | 2347864 | 9/2000 |

OTHER PUBLICATIONS

BHR Component Information; Midland Medical Technologies, Birmingham, B15 2SQ, England; 2002.
PCT Invitation to Pay Additional Fees mailed Jan. 13, 2006 for PCT/US2005/032788 (filed Sep. 15, 2004).

(Continued)

*Primary Examiner* — Alvin J Stewart

(57) ABSTRACT

A unitary acetabular cup prosthesis for a deficient acetabulum of a hip bone having a cup portion and a pair of adjacent screw retaining members extending from the cup and oriented in a cooperative with one another. A second pair of screw retaining members are preferably provided, with the first and second pair of screw retaining members oriented such that the prosthesis can be used in either a left or a right acetabulum of the patient. The screw retaining members may be formed on a single flange. The screw retaining members are fixedly inclined and offset relative to the rim of the cup. Each screw retaining member has a threaded hole inclined relative to the rim such that an axis of the threaded hole converges toward the axis of the cup portion in one dimension and is oblique to the axis of the cup portion in a second dimension.

20 Claims, 10 Drawing Sheets

OTHER PUBLICATIONS

International Search Report, PCT International Search Report mailed Apr. 21, 2006 for PCT/US2005/032788 (filed Sep. 15, 2004).

PCT Written Opinion of the International Searching Authority mailed Apr. 21, 2006 for PCT/US2005/032788 (filed Sep. 15, 2004).

* cited by examiner

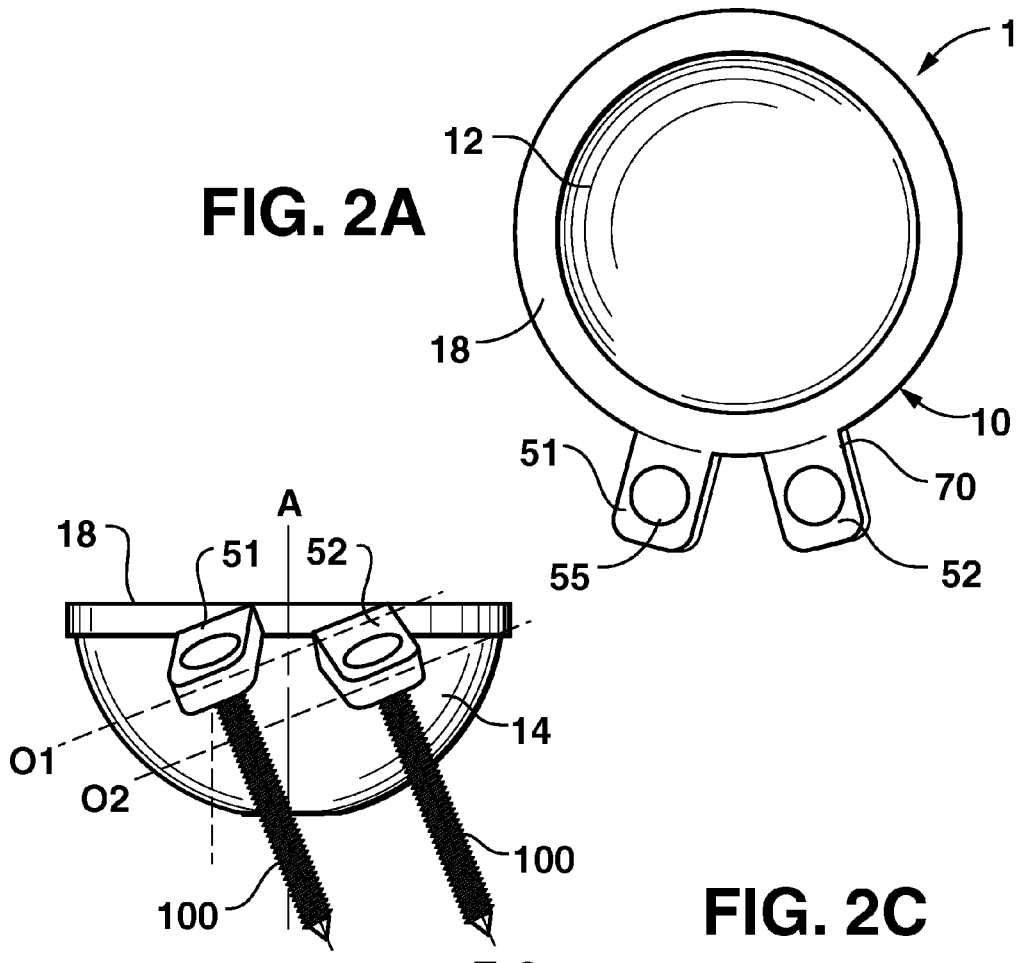
FIG. 2A
FIG. 2B
FIG. 2C
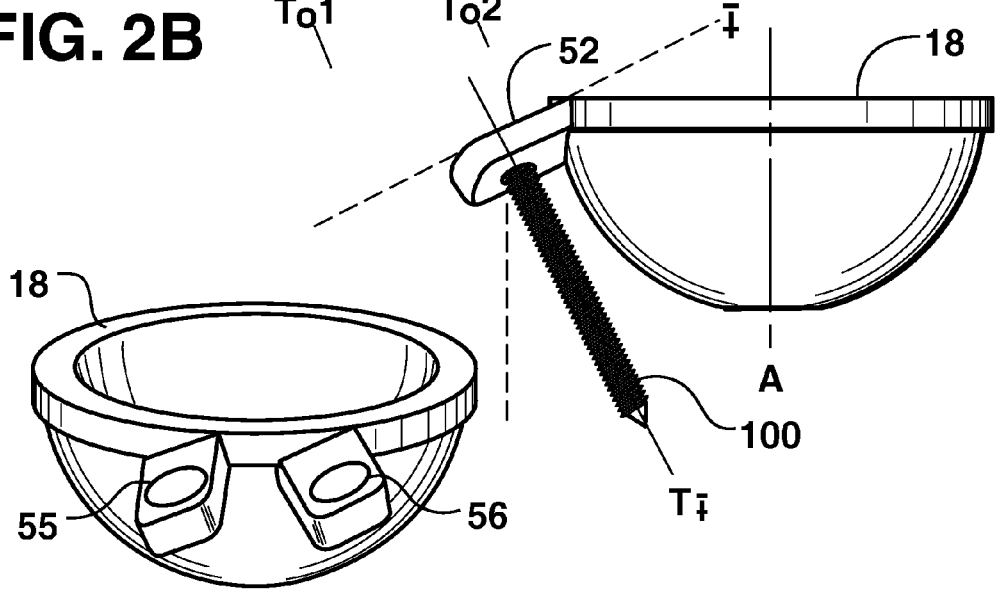
FIG. 2D

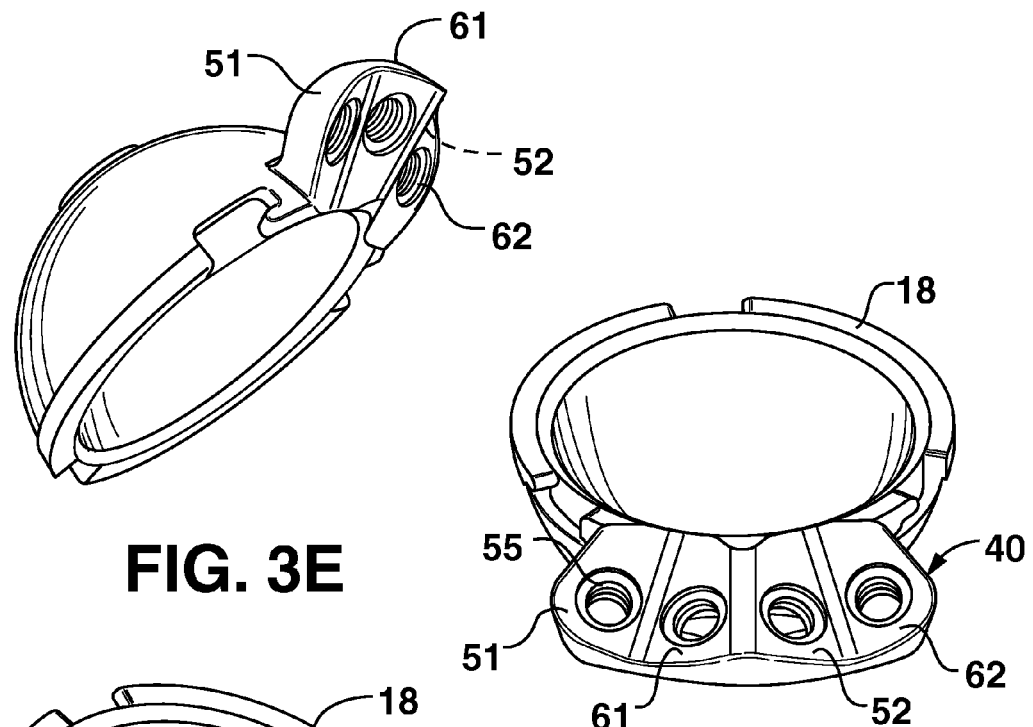
FIG. 3E
FIG. 3F
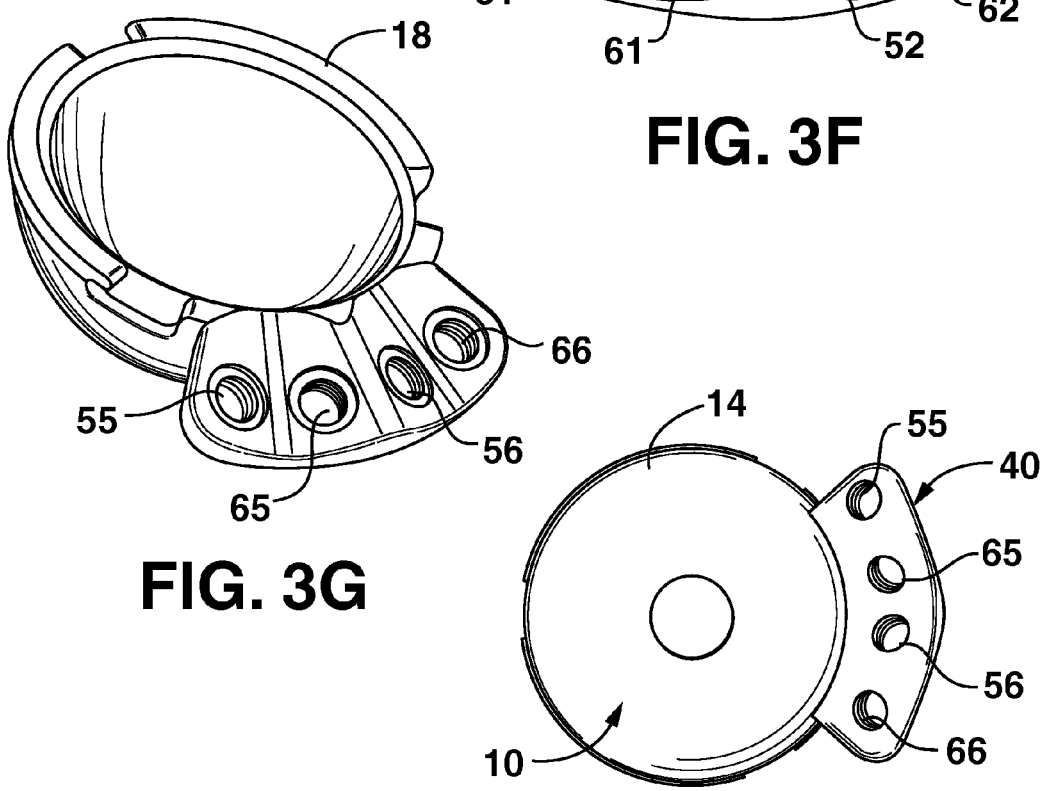
FIG. 3G
FIG. 3H

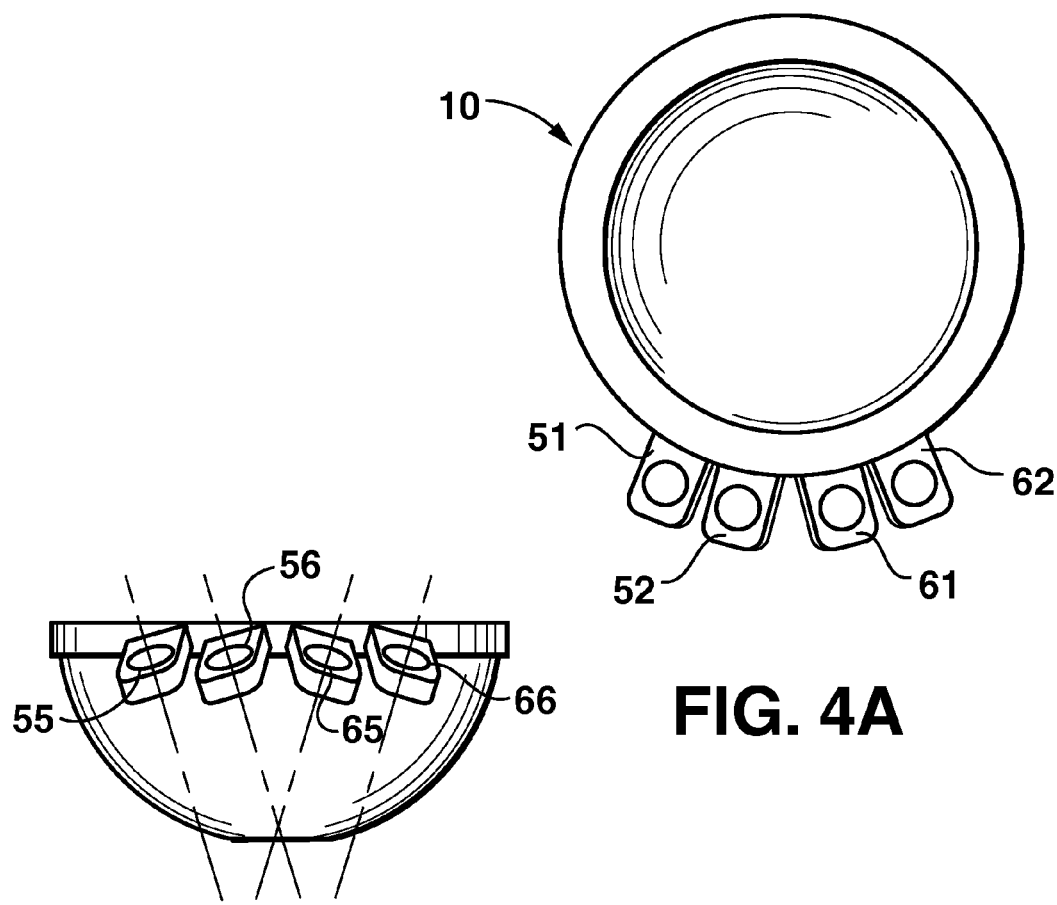
FIG. 4A
FIG. 4B
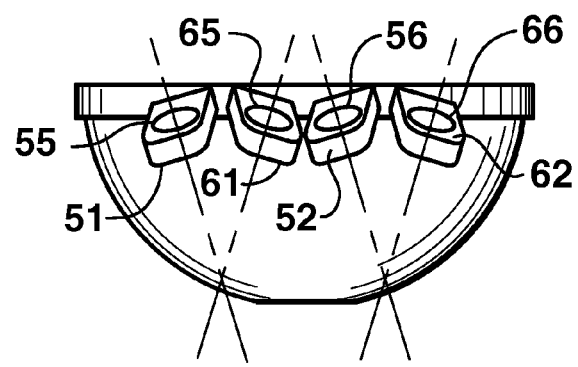
FIG. 4C

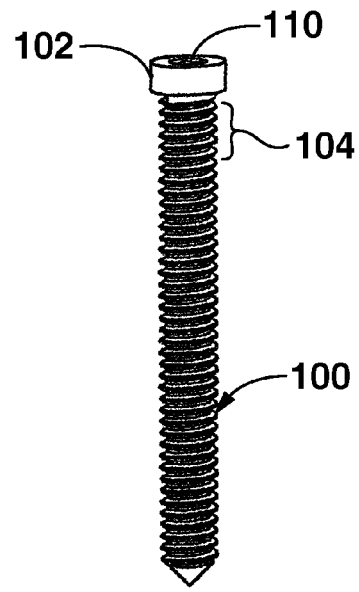
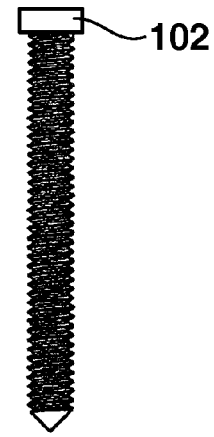
FIG. 5A     FIG. 5B
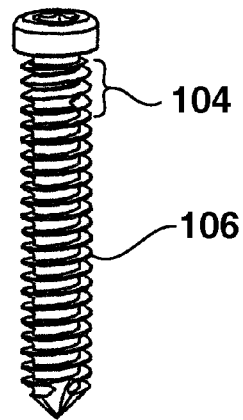
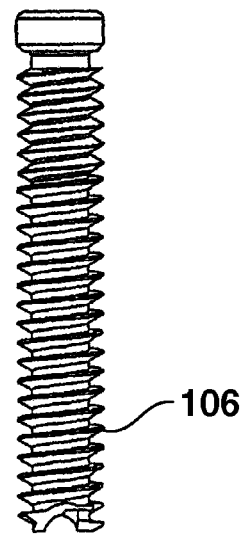
FIG. 5C     FIG. 5D

UNITARY ACETABULAR CUP PROSTHESIS WITH EXTENSION FOR DEFICIENT ACETABULUM

CROSS REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

FIELD OF THE INVENTION

The present invention relates to orthopedic prosthetic implants, and more particularly to an acetabular cup prosthesis that is configured particularly for treatment of deficient acetabula, such as the type encountered in hip dysplasia.

BACKGROUND OF THE INVENTION

Conventional acetabular cup prostheses employ a two-part construction comprising a cup portion and a separate bearing insert. The cup is secured in the acetabulum by one or more screws, which pass through the wall of the cup and directly into the bone of the acetabulum. Once the cup is secured, the bearing insert is installed in the cup. To prevent shifting or loosening of the cup, the acetabulum is reamed prior to cup insertion in order to provide a correct fit and a deeper pocket for the cup. To further improve stability, the cup is selected with a diameter large enough to span the widest part of the defect. The cup may also be selected to have a diameter slightly larger than that of the reamed acetabulum, such that a press-fit connection is achieved. However, a larger cup typically requires more reaming than a smaller cup, which may result in removal of viable as well as diseased bone.

Acetabular cup prostheses are used to correct various types of acetabular defects, including defects involving compromised acetabular walls or deficient bone. One type of acetabular defect is congenital hip dysplasia. In congenital hip dysplasia, portions of the rim of the acetabulum may be minimal and the acetabulum is shallower than normal. It is difficult to stabilize a cup prosthesis in a shallow acetabulum because little bone is available for reaming or for threading of screws.

Other deficient acetabular conditions may present problems similar to those encountered with dysplasia. In a revision hip replacement, loosening of the primary prosthesis or removal of bone cement often causes defects in the acetabulum. Infection may cause bone loss that results in a deformed or deficient acetabulum. Following a fracture, an acetabulum may heal in a deformed shape. In each of these situations, it may be desirable to minimize reaming and maximize use of available drillable bone in order to secure the prosthesis.

Conventional prostheses do not provide for secure fixation in deficient hips, such as those encountered in dysplasia, where there is not sufficient bone to allow for proper reaming and threading of screws. An inherent problem of prior art cups is a limited ability to be provided with fixation other than directly through the cup and into the acetabulum. To overcome this problem, attempts have been made to provide cups having an extension portion for use in securing the cup to available bone.

The prior art includes two-part acetabular cup prostheses that include rim extensions for use in securing the cups in deficient acetabula, such as the type encountered in congenital hip dysplasia. See U.S. Pat. No. 5,702,477 (Capello et al.); U.S. Pat. No. 5,931,870 (Cuckler); U.S. Pat. No. 6,162,257 (Gustilo et al.). These devices include screw holes in both the cup portion and the extension portion, such that the cup can be secured directly to the acetabulum and the extension portion can be secured directly to the surrounding bone, thus enhancing prosthesis stability even in deficient bone conditions.

U.S. Pat. No. 4,801,300 (Kurze et al.) recognized limitations in the ability of two-part hip prostheses to treat dysplasia hips. (Column 1, lines 41-42). To overcome this deficiency, Kurze et al. proposed a single-part hip joint socket provided with a perforated flange ring for mooring by implant screws. The flange covers at least two-thirds of the circumference of the hip joint socket. The flange has at least four uniformly distributed bore holes for receiving screws for securing the device on bone. The holes are unthreaded. Kurze et al. is directed primarily toward surface texturing for improving biocompatibility and mechanical stability. Kurze et al. provides no discussion of how the socket would be secured by screws. A disadvantage of Kurze et al. is that it does not provide for angulation of screws into available drillable bone in some deficient bone conditions.

FIG. 1 shows a prior art acetabular cup prostheses that is designed particularly for treatment of a dysplasic acetabulum. As shown in FIGS. 1A and 1B, the prior art cup has a pair of tabs that extend from an outer surface of the cup. Each tab includes a threaded hole for receiving a threaded screw for using in securing the cup in an acetabulum. As shown in FIGS. 1A and 1B, the tabs extend in the same plane as the rim of the cup, and are thus perpendicular to the axis of the cup. As shown in FIGS. 1A and 1B, the axis of each screw hole is parallel to the axis of the cup. One advantage of the acetabular cup of FIG. 1 is that it has a symmetrical configuration, and therefore can be used in either a left or right hip. However, a disadvantage of the acetabular cup of FIG. 1 is that the screws are oriented in a manner that does not maximize use of available drillable bone in some deficient bone conditions, such as those encountered in dysplasia.

GB Patent Application 2,347,864 (Paling) discloses a removeable attachment member that can be used to transform a conventional acetabular cup into a dysplasia cup. A primary objective of Paling is to allow a surgeon to determine intraoperatively whether to use a conventional cup or to convert the cup into a dysplasia cup. To accomplish this objective, Paling discloses an annular portion that is removably mountable on a rim of an acetabular cup and which has one or more integral flanges, each flange having a hole for receiving a screw. In order to negate the resultant moment imparted to the cup through the screws, the annular portion is preferably provided with two diametrically opposed flanges. Additionally, the two flanges are preferably angled relative to the annular portion. The flange angle is at a declination of 20 degrees or substantially 20 degrees from the underside of the annular portion. According to Paling, angulation allows a higher clamping force to be imparted by the ring when acting on the acetabular cup. However, as shown in FIG. 4 of Paling, the axes of the holes remains parallel to the axis of the cup, and thus do not provide for angled threading into bone. Paling discloses mounting the cup portion in the acetabulum in the conventional manner, followed by attachment of the annular portion to the cup portion such that projections on the annular portion engage recesses in the rim of the cup portion. Screws are then passed through the holes and into bone, such that the annular portion secures the acetabular cup in place. One disadvantage of Paling is that the annular portion is of thin construction, and therefore subject to potential failure. Additionally, because the annular portion is not fixed to the cup portion, there are circumstances in which the annular portion may separate or dislodge from the cup. Further, even in the angulated version of Paling, the screws are not angled so as to maximize use of available drillable bone in some deficient hip conditions.

There is thus a need for a acetabular cup prosthesis having the following characteristics and advantages over the prior art.

OBJECTS AND SUMMARY OF THE INVENTION

It is an object of the invention to provide an acetabular cup prosthesis configured to provide secure implantation in a deficient hip, such as a dyslasic hip.

It is an object of the invention to provide an acetabular cup prosthesis that maximizes the use of available bone in a deficient hip to provide improved stability.

It is an object of the invention to provide an acetabular cup prosthesis customizes the fit and stability of the cup in deficient acetabulae without requiring excessive reaming of good bone surrounding the deficiency.

It is an object of the invention to reduce inventory by providing a cup prosthesis that can be used in either a right or left acetabulum of a patient.

The foregoing objects and advantages are obtained by providing a unitary acetabular cup prosthesis for use in a deficient acetabulum of a hip bone of a patient having a cup portion and a pair of adjacent screw retaining members oriented for use in attaching the prosthesis to the patient's hip bone. The cup portion has a generally dome-shaped wall having an axis and an upper rim. An inner bearing surface of the wall is configured to pivotally engage a femoral head of a hip prosthesis. Each screw retaining member extends from an outer surface of the dome substantially along the rim. The screw retaining members are integrally formed with the cup portion such that the screw retaining members are fixedly inclined relative to the rim and fixedly offset relative to the rim. The screw retaining members are oriented in a cooperative relationship with one another to facilitate implantation of the prosthesis in one side of the hip of the patient. Each screw retaining member has a threaded hole therethrough. Each threaded hole is fixedly inclined relative to the rim such that an axis of the threaded hole converges toward the axis of the cup portion in one dimension and such that the axis of the threaded hole is oblique to the axis of the cup portion in a second dimension. To reduce prosthesis inventory, a second pair of screw retaining members may be provided, with the first and second pair of screw retaining members oriented such that the prosthesis can be used in either a left or a right acetabulum of the patient.

In one preferred embodiment, first and second pairs of screw retaining members are formed on a single flange. The flange extends from an outer surface of the dome substantially along a portion of the rim. The flange is integrally formed with the cup portion and is inclined relative to the rim. The first pair of screw retaining members are fixed in a cooperative relationship with one another to facilitate implantation of the device in a left hip of the patient. The second pair of screw retaining members are fixed in a cooperative relationship with one another to facilitate implantation of the device in a right hip of the patient, but in an oblique relationship with the first pair of screw retaining members. The first and the second pair of screw retaining members are preferably arranged in a staggered relationship.

The foregoing and other objects, features, aspects and advantages of the invention will become more apparent from the following detailed description of the invention when considered in conjunction with the accompanying drawings.

BRIEF DESCRIPTION OF THE DRAWINGS

FIG. 2A is a top view of one preferred embodiment of the acetabular cup prosthesis of the invention.

FIG. 2B is a side view of the cup of FIG. 2A, showing screws having a generally parallel cooperative orientation in an offset dimension.

FIG. 2C is a side perspective view of the cup of FIG. 2B, rotated approximately 90 degrees from FIG. 2B to show inclination of the screw in an inclined dimension.

FIG. 2D is perspective view of the cup of FIGS. 2A-2C.

FIG. 3E is a perspective view of the cup of FIGS. 3A-3H, with the cup angled to indicate a preferred orientation of the cup in a left hip of a patient when viewed from the front of the patient along the median sagittal plane.

FIG. 3F is a perspective view of the preferred embodiment of FIGS. 3A-3H, rotated approximately 45 degrees forward from FIG. 3B.

FIG. 3G is a further perspective view of the preferred embodiment of FIGS. 3A-H.

FIG. 3H is a bottom view of the preferred embodiment of FIGS. 3A-3H.

FIGS. 4A-4C show views of one preferred embodiment of the acetabular cup prosthesis of the invention configured for use in either a left or a right hip of a patient.

FIG. 5 provides views of preferred embodiments threaded screws for use with the acetabular cup prosthesis of the invention.

PREFERRED EMBODIMENTS OF THE INVENTION

Figure 1A:
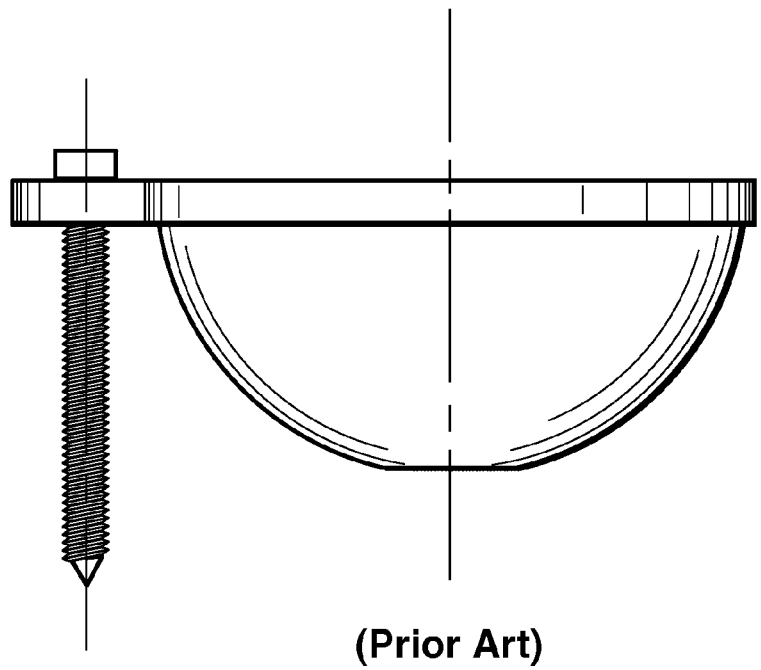
FIG. 1A is a side view of a prior art dysplasia cup, featuring a retaining screw oriented in a parallel relationship with the axis of the cup.

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

As shown in FIG. 2, the invention is a unitary acetabular cup prosthesis 1 for use in a deficient acetabulum of a hip of a patient. The prosthesis 1 includes a cup portion 10. As shown in FIG. 2B, the cup portion 10 has a generally dome-shaped wall 10 having an axis A and an upper rim 18. As indicated in FIG. 2A, an inner bearing surface 12 of the wall 10 is configured to pivotally engage a femoral head of a femoral hip prosthesis, in a manner known to those of skill in the art. As indicated in FIG. 2B, an outer surface 14 of the dome 10 is sized and configured to reside at least partially within the acetabulum of the patient, in a manner known to those of skill in the art.

As shown in FIG. 2, a pair of first and second screw retaining members 51, 52 are provided for use in attaching the prosthesis to the patient's hip. As shown in FIG. 2B, each screw retaining member extends from the outer surface 14 of the dome 10 substantially along the rim 18. As shown in FIG. 2C, the screw retaining members 51, 52 are integrally formed with the cup portion 10 such that each screw retaining member 51, 52 is fixedly inclined relative to the rim 18. The inclination orientation is shown with reference to line or plane "I" in FIG. 2C. As indicated in FIG. 2C, inclination enables screws 100 to be located as close as possible to the outer surface 14 of the cup portion 10, an orientation that maximizes use of drillable bone in a dysplasic hip. Additionally, as further shown in FIG. 2B, the screw retaining members 51, 52 are also fixedly offset relative to the rim 18. The offset orientation is shown with reference to line or plane "O1" and "O2" in FIG. 2B. As shown in FIGS. 2B and 2C, the screw retaining members 51, 52 are oriented in a cooperative relationship with one another to facilitate implantation of the prosthesis 1 in one side of the hip of the patient.

In a preferred embodiment, each screw retaining member 51, 52 is inclined at an angle of between about 10 and about 25 degrees relative to the rim 18 (see FIG. 2C). In a most preferred embodiment, each screw retaining member 51, 52 is fixedly inclined at an angle of about 20 degrees relative to the rim 18. In a preferred embodiment, each screw retaining member 51, 52 is offset at an angle of between about 10 and about 25 degrees relative to the rim 18 (see FIG. 2B). In a most preferred embodiment, each screw retaining member 51, 52 is fixedly offset at an angle of about 20 degrees relative to the rim 18.

As shown in FIGS. 2B, 2C and 2D, each screw retaining member 51, 52 has a threaded hole 55, 56 therethrough. Each threaded hole 55, 56 is fixedly inclined relative to the rim 18 such that an axis of the threaded hole ($T_I$) converges toward the axis (A) of the cup portion in one dimension (see FIG. 2C), and such that the axis of the threaded hole ($T_O1$; $T_O2$) is oblique to the axis (A) of the cup portion in a second dimension (see FIG. 2B).

As indicated in FIGS. 2, 3 and 4, the screw retaining members 51, 52 are adjacent to one another in order to maximize anchorage in the area of drillable bone. The screw retaining members 51, 52 preferably extend along an arc of between about 30 to about 60 degrees along the circumference of the rim 18. If two sets of screw retaining members 51, 52, 61, 62 are provided (discussed in further detail below), the screw retaining members 51, 52, 61, 62 preferably occupy an arc of less than about 90 degrees along the circumference of the rim 18, and preferably of about 75 degrees. As also indicated in FIG. 2B, the screw retaining members 51, 52 are preferably spaced apart a selected distance, such as about 10 mm (or an arc of between about 15 to 25 degrees, depending on the size of the prosthesis). Spacing of the screw holes 55, 56 provides greater stability to the cup 1 when the prosthesis is implanted in an acetabulum. However, in situations where only a very small area of drillable bone is available, it may be preferable to have the screw retaining members 51, 52 directly adjacent to one another. For added strength, the first and second screw retaining members 51, 52 may be joined to one another, such as in the manner shown in FIG. 3.

Figure 2E:
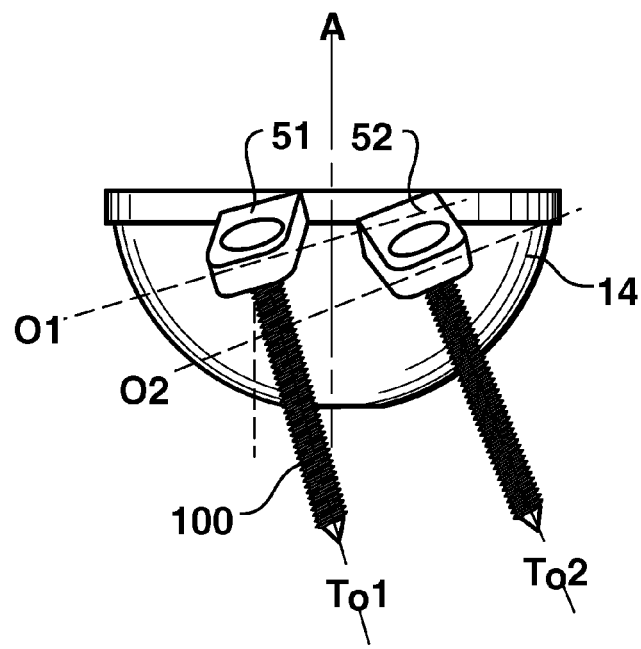
FIG. 2E is a side view of one preferred embodiment of the acetabular cup prosthesis of the invention showing screw retaining members that are slightly divergent from one another in the offset orientation, such that the screws have a toed-out or oblique relationship to one another.
Figure 2F:
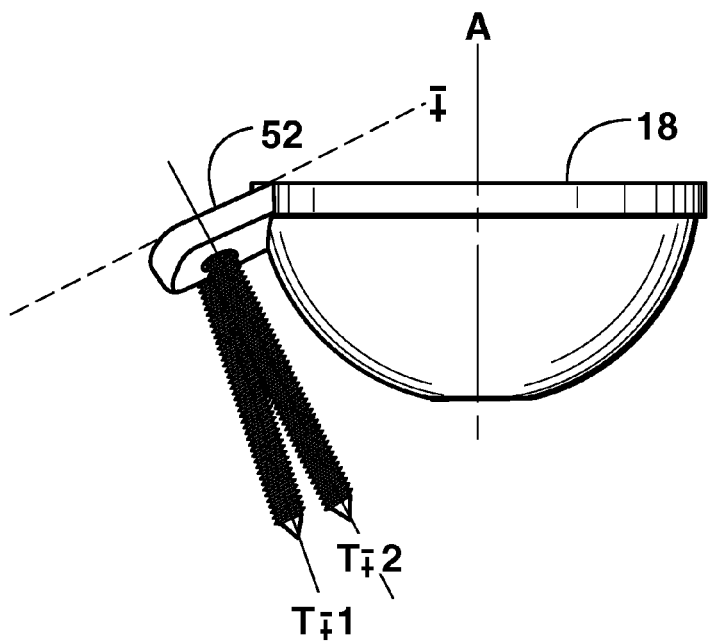
FIG. 2F is a side view of the cup of FIG. 2E rotated approximately 90 degrees from FIG. 2E to show screws in a toed-out or oblique relationship to one another.

As shown in FIG. 2B, to provide cooperative fixation between the screw retaining members 51, 52, the screw retaining members may be oriented in a generally parallel relationship with one another (compare line/plane O1 with line/plane O2). Likewise, as also shown in FIG. 2B, the threaded holes 55, 56 of the pair of screw retaining members 51, 52 may be in a parallel relationship with one another (compare thread/fixation axes $T_O1$ and $T_O2$). A substantially parallel orientation of the threaded holes 55, 56 enables fixation about two generally parallel fixation axes in the patient's acetabulum. In some deficient hip conditions, a parallel orientation may contribute to maximal use of available bone, along with greater resistance to the forces encountered in the hip. However, in many applications it may be desirable to orient the screws 100 in a divergent or oblique orientation in relation to each other as shown in FIG. 2E or 2F. A divergent orientation contributes greater pull-out strength to the screws and greater stability to rotational moments encountered in the hip joint. The divergent orientation includes toe-out and toe-in (technically, convergent) orientations. As shown most clearly in FIG. 2E, a divergent orientation can be accomplished by orienting the screw retaining members in an oblique relationship to one another, either in the offset dimension, in the inclination dimension or, preferably, in both offset and inclination dimensions. In some cases, the divergent orientation will be generally, but not precisely, parallel.

As indicated in FIG. 2C, the axis of the threaded hole 55, 56 of the retaining members 51, 52 is preferably substantially perpendicular to the inclination of the screw retaining member 51, 52 (compare inclination thread/fixation axes $T_I$ with inclination line/plane I). As further indicated in FIG. 2B, the axis of the threaded hole 55, 56 of the retaining members 51, 52 is also preferably substantially perpendicular to the offset of the screw retaining member 51, 52.

One disadvantage of the embodiment shown in FIG. 2 is that the prosthesis can only be used in one side of a patient's hip, due to the cooperative inclination and offset orientations of the screw receiving members 51, 52. It is an object of the invention to reduce inventory by providing a cup prosthesis 1 that can be used in either a right or left acetabulum of a patient. This objective can be achieved by providing a second set of screw retaining members 61, 62, such as in the embodiment shown in FIG. 4A (see also FIG. 3). The second set of screw retaining members 61, 62 includes the orientations and characteristics described above with regard to the first set of screw retaining members 51, 52. However, as shown in FIG. 4B, the second set of screw retaining members 61, 62 is fixed in a substantially opposite or mirrored orientation in relation to the first set of screw retaining members 51, 52. In the embodiment shown in FIG. 4B, the first set of screw retaining members 51, 52 are directly adjacent to one another, while the second set of screw retaining members 61, 62 are directly adjacent one another. In the embodiment shown in FIG. 4C, the first and second sets of screw retaining members are in a staggered relationship in which the screw retaining members of the first set 51, 52 alternate with screw retaining members of the second set 61, 62. One advantage of the staggered embodiment shown in FIG. 4C is that it allows the cooperative screw retaining members of each set to be spaced apart from one another, yet occupy a minimal arc along the rim 18. Note that in each case, the first pair of screw retaining members 51, 52 are oriented in a cooperative relationship with one another to facilitate implantation of the prosthesis in one side of the hip of a patient, while the second pair of screw retaining members 61, 62 are oriented in a cooperative relationship with one another to facilitate implantation of the prosthesis 1 in the opposing hip of the patient. In this manner, required inventory is reduced.

FIG. 3 shows a preferred embodiment of a unitary acetabular cup that can be used in either a right or left deficient acetabulum of a patient. As shown most clearly in FIGS. 3A and 3C, a flange 40 extends from the outer surface 14 of the dome 10 substantially along a portion of the rim 18. The flange 40 is integrally formed with the cup portion 10. As shown in FIG. 3C, the flange 40 is inclined relative to the rim 18. The flange is preferably inclined at between about 10 to 25 degrees relative to the rim 18. In the preferred embodiment shown in FIG. 3, the flange 40 is inclined at about 20 degrees relative to the rim 18.

Figure 3A:
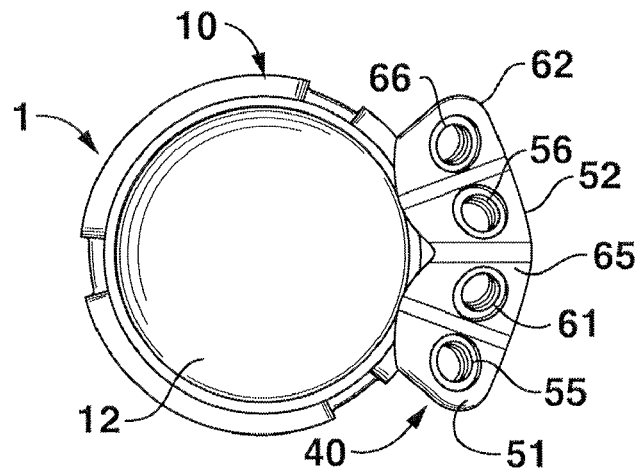
FIG. 3A is a top view of one preferred embodiment of the acetabular cup prosthesis of the invention configured for use in either a left or a right hip of a patient.

As shown in FIG. 3A, the flange 40 includes a first 51, 52 and a second 61, 62 pair of screw retaining members formed thereon for use in attaching the prosthesis to the patient's hip bone. The screw retaining members 51, 52, 61, 62 include the orientations and characteristics described above with reference to FIG. 2, except that the screw retaining members 51, 52, 61, 62 are oriented on a single flange 40. For example, as shown most clearly in FIG. 3B, each screw retaining member 51, 52, 61, 62 is fixedly inclined relative to the rim 18 and also fixedly offset relative to the rim 18. As shown in FIG. 3A, each screw retaining member has a threaded hole 55, 56, 65, 66 therethrough. As indicated in FIG. 3C, each threaded hole 55, 56, 65, 66 is fixedly inclined relative to the rim 18 such that an axis of the threaded hole converges toward the axis of the cup portion 10 in one dimension, in the manner described above with reference to FIG. 2C. Likewise, as indicated in FIG. 3B, the axis of each threaded hole is oblique to the axis of the cup portion in a second dimension (see thread lines/axes T1, T2, T3, T4), in the manner described above with reference to FIG. 2B.

Figure 3B:
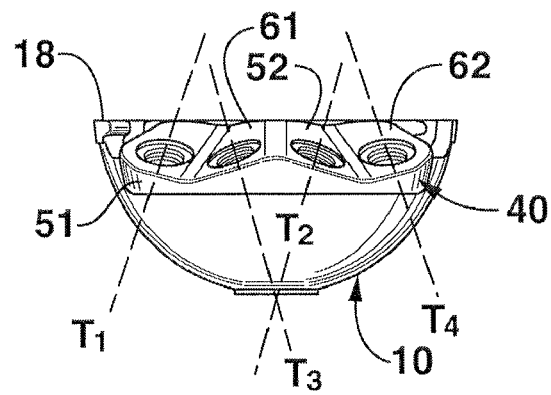
FIG. 3B is a side view down the flange portion of FIG. 3A, featuring orientation of two sets of screw retaining members on the flange, and indicating offset orientation of the threaded bores.
Figure 3C:
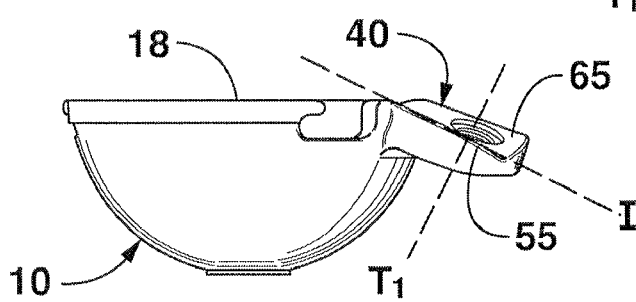
FIG. 3C is a side view of the cup of FIG. 3B, rotated approximately 90 degrees from FIG. 3B to show inclination the flange and an inclined orientation of the threaded bores.

As shown in FIG. 3B, the first pair of screw retaining members 51, 52 are fixed in a substantially parallel relationship with one another, and the second pair of screw retaining members 61, 62 are also fixed in a substantially parallel relationship with one another. As shown in FIG. 3B, the first 51, 52 and second 61, 62 sets of screw retaining members are also fixed in an oblique relationship to one another, such that the prosthesis can be used on either a left or right acetabulum, in the manner described above. In the embodiment shown in FIG. 3, the first 51, 52 and the second 61, 62 pair of screw retaining members arranged in a staggered relationship, a configuration that minimizes the degree of arc required by the flange 40.

As indicated in FIG. 3B, the threaded holes 55, 56 of the first pair of screw retaining members 51, 52 are preferably in a substantially parallel relationship with one another (compare thread line/axes T1 and T2). Likewise, the threaded holes 65, 66 of the second pair of screw retaining members 61, 62 are in a substantially parallel relationship with one another (compare thread lines/axes T3 and T4). As shown in FIG. 3B, the threaded holes 55, 56 of the first pair of screw retaining members 51, 52 are in an oblique relationship with the threaded holes 65, 66 of the second pair of screw retaining members 61, 62, an orientation that enables the prosthesis 1 to be used on either a left or a right acetabulum of the patient.

As further indicated in FIG. 3C, the axis T1 of the threaded hole 55 of each screw retaining member 51 is preferably substantially perpendicular to the inclination I of the screw retaining member 51. As indicated in FIG. 3B, the axis of the threaded hole 55 of each screw retaining member 51 is also preferably substantially perpendicular to the offset of the screw retaining member 51 (compare thread lines/axes T1, T2, T3 and T4 with the lower face of the corresponding screw retaining member).

Figure 7A:
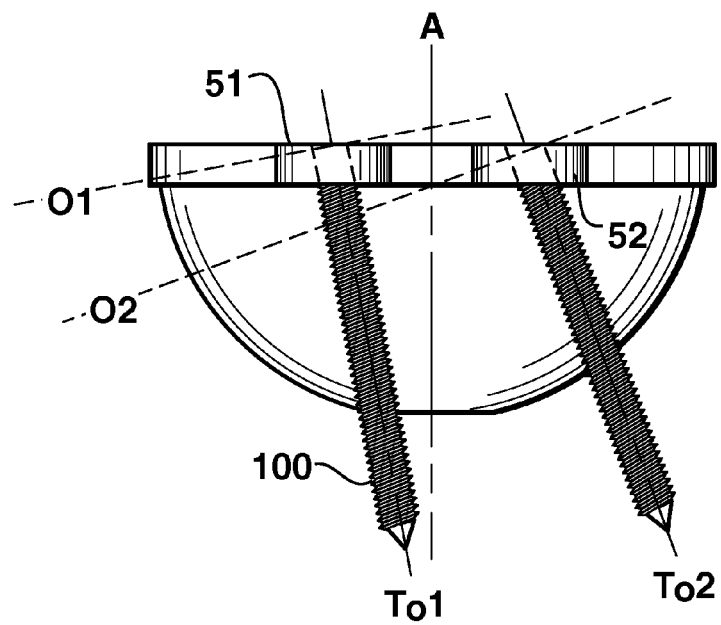
FIG. 7A is a side view of an alternative embodiment of the invention in which an offset orientation is provided by angulation of threaded bores alone.
Figure 7B:
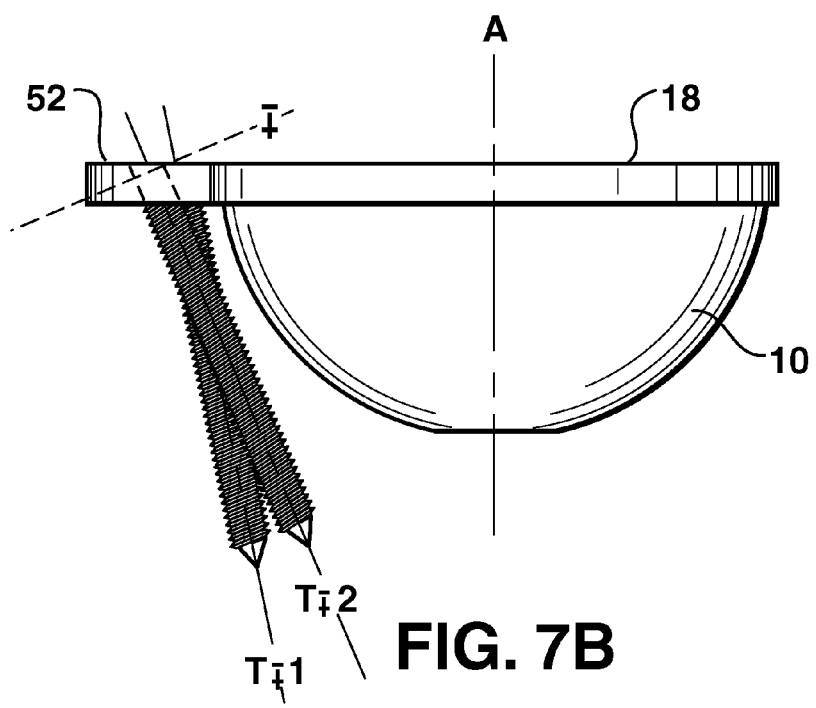
FIG. 7B is a side view of the cup of FIG. 2E rotated approximately 90 degrees from FIG. 7A to show an inclined orientation provided by angulation of threaded bores alone.

FIGS. 7A and 7B show an alternative embodiment in which inclination and offset are provided through inclination and offset of the threaded bores alone, rather than by inclination and offset of the screw retaining portions 51, 52. As shown in FIG. 7B, the embodiment employs squarely oriented screw retaining members 52 that extend substantially in the plane of the rim 18, i.e. substantially perpendicular to the axis A of the cup 10. As indicated in FIGS. 7A and 7B, the various offset and inclination angles discussed above can be obtained with this embodiment. However, the screw retaining member 51, 52 must project further laterally in order to obtain desired degrees of inclination. The squarely oriented retaining members 51, 52 could be provided on a single flange. A pair of squarely oriented retaining members 51, 52, 61, 62 could also be provided on a single flange 40 (not shown). It is also possible to provide offset retaining members having inclined bore holes or inclined retaining members having offset bore holes. Further, the inclined and offset angles of screws discussed above can be provided by using selected combinations of square, inclined, or offset retaining members and applicably oriented thread bores.

Figure 1B:
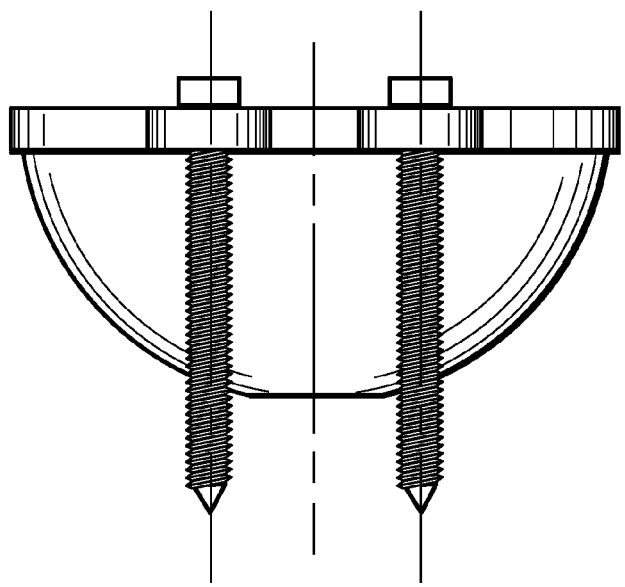
FIG. 1B is a side view of the prior art dysplasia cup of FIG. 1, rotated 90 degrees to the show the orientation of a pair of screws in screw retainer portions, the screws being parallel to the axis of the cup.

The prior art dysplasia cup shown in FIG. 1 employs screws having machine threads having a generally uniform pitch. FIGS. 5A-5B show a screw 100 for use in the invention that includes a machine thread as well as a head 102 configured to be countersunk in the screw retaining members 51, 52. To improve screw performance, the screws 100 are preferably provided with a bone screw thread, such as a cancellous bone thread, along a distal portion of the screw shaft for optimal threading in bone, and a machine thread along a proximal portion of the shaft 104 adjacent the screw head 102 for optimal threading in the threaded bore (FIGS. 5C-5D). The bone thread preferably has a distal pitch of 30 degrees and a proximal pitch of 3 degrees. The thread in the proximal portion 104 of the shaft closely matches the thread of the screw bore in order to provide a locking fit. To further enhance locking between the screw 100 and the threaded bore, a locking means such as double lead threads or mismatched threads may be used.

The prosthesis 1 is preferably made of a titanium alloy or a cobalt chromium, although various known materials may be suitable. Optionally, the outer surface 14 of the cup portion 10 has a controlled-porosity surface to enable bone growth to the prosthesis 1. The outer surface 14 may also be associated with a biologically active agent that enhances bone growth (e.g. bone-morphogenetic protein; growth factors; hydroxyapatite) to encourage bone growth to the prosthesis 1.

Various advantages arise from the configuration of the acetabular cup prosthesis 1, some of which are discussed above. The unique configuration of the acetabular cup prosthesis 1 enables it to be used as both a primary or a revision implant. The prosthesis provides for metal-on-metal articulation, resulting in minimal debris versus metal-on-UHMWPE prostheses. The invention 1 provides a rigid construct in which the angle of the screws is maintained, thus enabling the screws to maintain the cup 10 in position. The thin phalange 40 provides sufficient strength without impinging on implantation of the device.

Figure 3D:
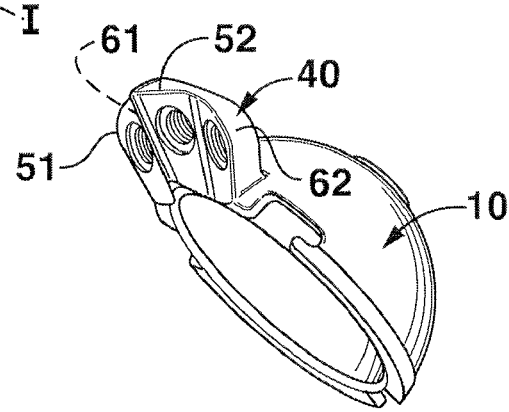
FIG. 3D is a perspective view of the cup of FIGS. 3A-3H, with the cup angled to indicate a preferred orientation of the cup in a right hip of a patient when viewed from the front of the patient along the median sagittal plane.
Figure 6A:
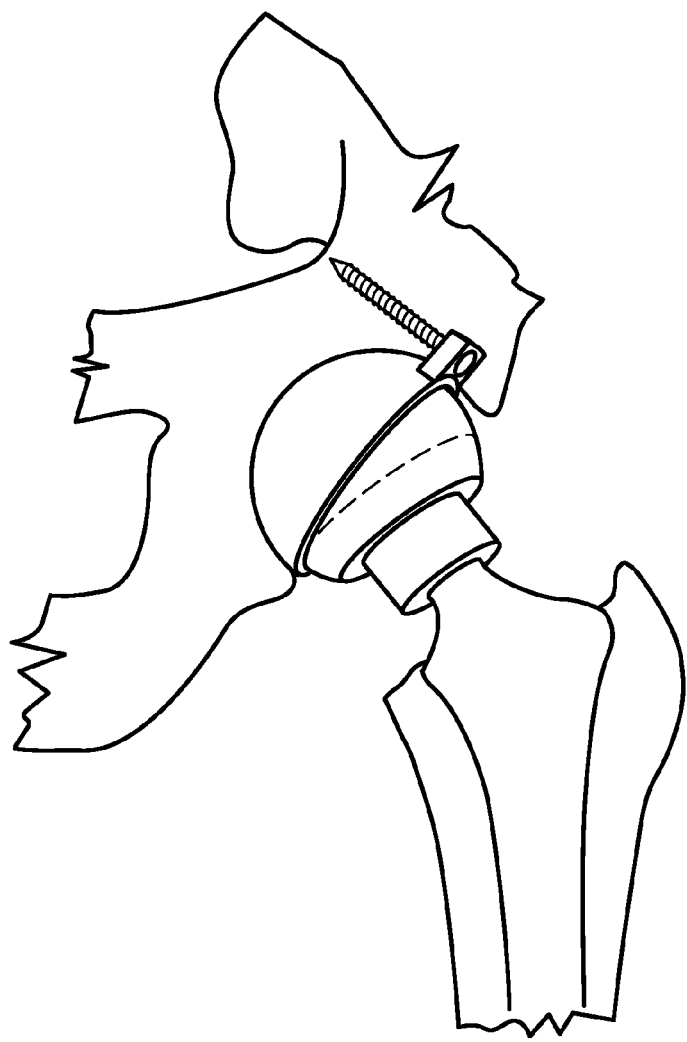
FIG. 6A is an x-ray view of the prior art dysplasia cup of FIG. 1 installed in a dysplasic hip of a patient, and indicating undesirable retroversion of the cup along the flat contour of the dysplasic hip.
Figure 6B:
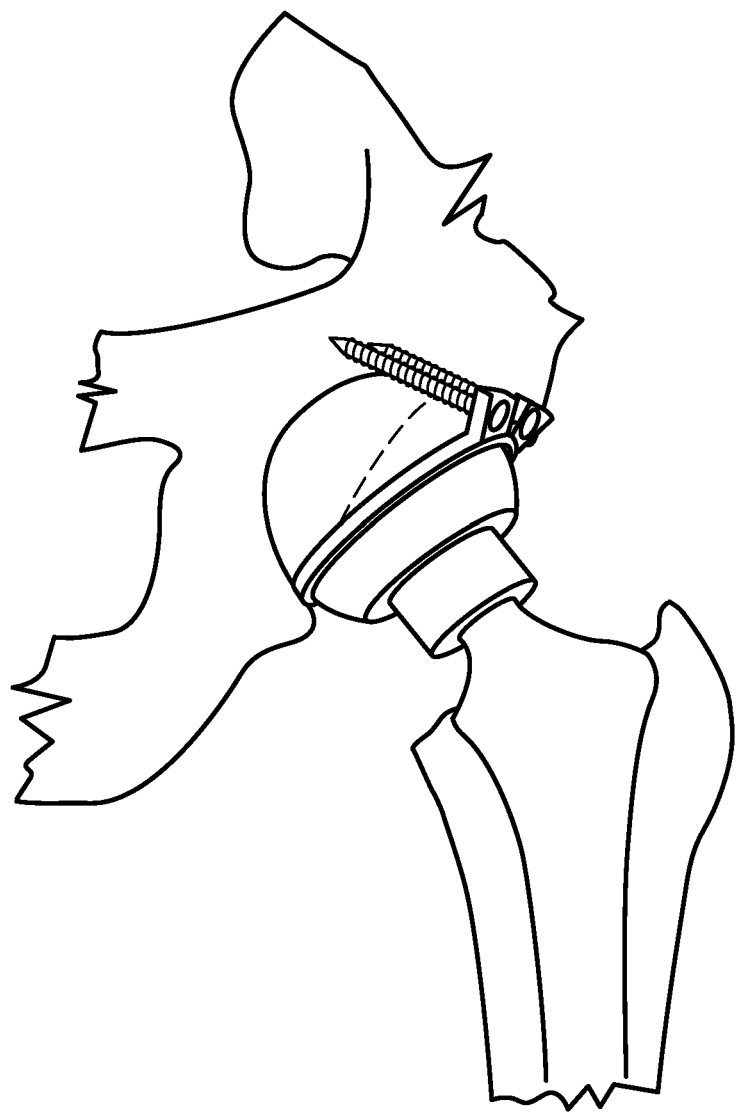
FIG. 6B is an x-ray view of one preferred embodiment of the acetabular cup prosthesis of the invention installed in a deficient hip of a patient, indicating a preferred degree of anteversion of the cup versus prior art dysplasia cups such as the prior art cup shown in FIG. 6A.

Although the invention has been described as a unitary cup embodiment, the internal wall 12 of the cup 10 may alternatively be configured to receive an insert configured to articulate with the femoral head of femoral hip prosthesis, such as an UHMWPE or ceramic insert In operation, the acetabular cup prosthesis 1 is installed in a patient in much the same manner as a conventional cup or dysplasia cup. However, because of the unique angulation of the threaded bores, the cup 1 of the invention can be installed in a greater degree of anteversion or retroversion compared to conventional dysplasia cups, such as the type shown in FIG. 1. As mentioned above, the flat contour and generally thinner cross-section of a dysplasic hip provides minimal bone for reaming or screwing, which makes it difficult to orient a cup in a sufficiently anteverted position. FIG. 6A provides an x-ray view of the prior art dysplasia cup of FIG. 1 installed in a dysplasic hip of a patient. Because of the location of the screws, the prior art cup must often be implanted in a somewhat retroverted position in order obtain a firm setting in available drillable bone, which can contribute to a dislocation. A phantom line along the femoral prosthesis head in FIG. 6A indicates a preferred position of the rim of the cup relative to the hip and the femoral prosthesis. FIG. 6B is an x-ray view of one preferred embodiment of the acetabular cup prosthesis 1 of the invention installed in a deficient hip of a patient. In FIG. 6B, the cup 1 is fixed in an orientation that is substantially identical to the desired position of a prosthesis in a non-dysplasic hip, and which thus minimizes the risk of dislocation. The phantom line in FIG. 6B indicates a typical position of the rim of prior art dysplasic cups in a dysplasic hip. FIG. 3D is a perspective view of the cup of FIGS. 3A-3H, with the cup angled to indicate a preferred orientation of the cup in a right hip of a patient when viewed from the front of the patient along the median sagittal plane. FIG. 3E is a perspective view of the cup of FIGS. 3A-3H, with the cup angled to indicate a preferred orientation of the cup in a left hip of a patient when viewed from the front of the patient along the median sagittal plane. While exact orientations will vary from patient to patient, the prosthesis of the invention 1 will preferably be installed such that the rim 18 of the cup 1 is fixed at about 45 degrees relative to vertical and about 15 to 20 degrees anteversion, generally in the orientations shown in FIGS. 3D and 3E.

In order to minimize stability problems, a drill guide is preferably used to drill holes and insert the screws into the hip.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A unitary acetabular cup prosthesis for use in a deficient acetabulum of a hip bone of a patient, the prosthesis comprising:

a cup portion comprising a generally dome-shaped wall having an axis and an upper rim, an inner bearing surface of said wall configured to pivotally engage a femoral head of a hip prosthesis, a pair of adjacent screw retaining members for use in attaching the prosthesis to the patient's hip bone, each said screw retaining member extending from an outer surface of said dome substantially along said rim, each said screw retaining member integrally formed with said cup portion such that said screw retaining member is fixedly inclined relative to said rim and is fixedly offset relative to said rim, said screw retaining members oriented in a cooperative relationship with one another to facilitate implantation of the prosthesis in one side of the hip of the patient, and each said screw retaining member having a threaded hole therethrough, each said threaded hole fixedly inclined relative to said rim such that an axis of said threaded hole converges toward said axis of said cup portion in one dimension and such that said axis of said threaded hole is oblique to said axis of said cup portion in a second dimension.

2. The prosthesis of claim 1, wherein said threaded holes of said pair of screw retaining members are in a parallel relationship with one another to thereby enable fixation about parallel fixation axes in the patient's hip bone.

3. The prosthesis of claim 2, wherein said axis of said threaded hole of each said screw retaining member is substantially perpendicular to said inclination of said screw retaining member and substantially perpendicular to said offset of said screw retaining member.

4. The prosthesis of claim 1, wherein said threaded holes of said pair of screw retaining members are in a divergent relationship with one another to thereby enable fixation about non-parallel fixation axes in the patient's hip bone.

5. The prosthesis of claim 4, wherein said axis of said threaded hole of each said screw retaining member is substantially perpendicular to said inclination of said screw retaining member and substantially perpendicular to said offset of said screw retaining member.

6. The prosthesis of claim 1, wherein each said screw retaining member is fixedly inclined at an angle of between about 10 and about 25 degrees relative to said rim and each said screw retaining member is fixedly offset at an angle of between about 10 and about 25 degrees relative to said rim.

7. The prosthesis of claim 1, wherein each said screw retaining member is fixedly inclined at an angle of about 20 degrees relative to said rim and each said screw retaining member is fixedly offset at an angle of about 20 degrees relative to said rim.

8. The prosthesis of claim 1, further comprising a second pair of screw retaining members for use in attaching the prosthesis to the patient's hip bone, each said screw retaining member of said second pair extending from said outer surface of said dome substantially along said rim, each said screw retaining member of said second pair integrally formed with said cup portion such that said screw retaining member is fixedly inclined relative to said rim and is fixedly offset relative to said rim, said screw retaining members oriented in a cooperative relationship with one another to facilitate implantation of the prosthesis in an opposing side of the hip of the patient, each said screw retaining member of said second pair having a threaded hole therethrough, each said threaded hole fixedly inclined relative to said rim such that an axis of said threaded hole converges toward said axis of said cup portion in one dimension and such that said axis of said threaded hole is oblique to said axis of said cup portion in a second dimension, and said first and said second pairs of screw retaining members oriented such that the prosthesis can be used in either a left or a right acetabulum of the patient.

9. The prosthesis of claim 8, wherein said screw retaining members are formed on a single flange.

10. The prosthesis of claim 1, wherein said screw retaining members are formed on a single flange.

11. A method of implanting a prosthesis in a defective hip bone of a patient comprising:
providing a unitary acetabular cup prosthesis according to claim 1,
placing the unitary acetabular cup prosthesis in an acetabulum of the patient,
securing the unitary acetabular cup prosthesis in the hip bone by threading screws through the threaded holes of the screw receiving members and into the hip bone such that a rim of the prosthesis is maintained in an orientation of about 45 degrees relative to vertical.

12. A unitary acetabular cup prosthesis for use in a deficient acetabulum of a hip bone of a patient, the prosthesis comprising:
a cup portion comprising a generally dome-shaped wall having an axis and an upper rim, an inner bearing surface of said wall configured to pivotally engage a femoral head of a hip prosthesis,
a flange extending from an outer surface of said dome substantially along a portion of said rim, said flange integrally formed with said cup portion, said flange inclined relative to said rim,
said flange including a first and a second pair of screw retaining members formed thereon for use in attaching the prosthesis to the patient's hip bone,
each said screw retaining member fixedly inclined relative to said rim and fixedly offset relative to said rim,
each said screw retaining member having a threaded hole therethrough, each said threaded hole fixedly inclined relative to said rim such that an axis of said threaded hole converges toward said axis of said cup portion in one dimension and such that said axis of said threaded hole is oblique to said axis of said cup portion in a second dimension,
said first pair of screw retaining members fixed in a cooperative relationship with one another to facilitate implantation of the device in a left hip of the patient,
said second pair of screw retaining members fixed in a cooperative relationship with one another to facilitate implantation of the device in a right hip of the patient and in an oblique relationship with said first pair of screw retaining members, and
said first and said second pair of screw retaining members arranged in a staggered relationship.

13. The prosthesis of claim 12, wherein said threaded holes of said first pair of screw retaining members are in a generally parallel relationship with one another to thereby enable fixation about parallel fixation axes in the patient's acetabulum,
said threaded holes of said second pair of screw retaining members are in a generally parallel relationship with one another to thereby enable fixation about parallel fixation axes in the patient's acetabulum, and
said threaded holes of said first pair of screw retaining members are in an oblique relationship with said threaded holes of said second pair of screw retaining members.

14. The prosthesis of claim 13, wherein said axis of said threaded hole of each said screw retaining member is substantially perpendicular to said inclination of said screw retaining member and substantially perpendicular to said offset of said screw retaining member.

15. The prosthesis of claim 11, wherein said axis of said threaded hole of each said screw retaining member is substantially perpendicular to said inclination of said screw retaining member and substantially perpendicular to said offset of said screw retaining member.

16. The prosthesis of claim 12, wherein said threaded holes of said first pair of screw retaining members are in a divergent relationship with one another to thereby enable fixation about non-parallel fixation axes in the patient's acetabulum,
said threaded holes of said second pair of screw retaining members are in a divergent relationship with one another to thereby enable fixation about non-parallel fixation axes in the patient's acetabulum, and
said threaded holes of said first pair of screw retaining members are in an oblique relationship with said threaded holes of said second pair of screw retaining members.

17. The prosthesis of claim 16, wherein said axis of said threaded hole of each said screw retaining member is substantially perpendicular to said inclination of said screw retaining member and substantially perpendicular to said offset of said screw retaining member.

18. The prosthesis of claim 12, wherein each said screw retaining member is fixedly inclined at an angle of between about 10 and about 25 degrees relative to said rim and each said screw retaining member is fixedly offset at an angle of between about 10 and about 25 degrees relative to said rim.

19. The prosthesis of claim 12, wherein each said screw retaining member is fixedly inclined at an angle of about 20 degrees relative to said rim and each said screw retaining member is fixedly offset at an angle of about 20 degrees relative to said rim.

20. A method of implanting a prosthesis in a defective hip bone of a patient comprising:
providing a unitary acetabular cup prosthesis according to claim 12,
placing the unitary acetabular cup prosthesis in an acetabulum of the patient,
securing the unitary acetabular cup prosthesis in the hip bone by threading screws through the threaded holes of the screw receiving members and into the hip bone such that a rim of the prosthesis is maintained in an orientation of about 45 degrees relative to vertical.

* * * * *